United States Patent [19]
Gardetto et al.

[11] Patent Number: 5,370,649
[45] Date of Patent: Dec. 6, 1994

[54] LATERALLY REFLECTING TIP FOR LASER TRANSMITTING FIBER

[75] Inventors: William W. Gardetto, Bedford; Millard M. Judy; James L. Matthews, both of Dallas, all of Tex.

[73] Assignee: MyriadLase, Inc., Forest Hill, Tex.

[21] Appl. No.: 180,652

[22] Filed: Jan. 13, 1994

Related U.S. Application Data

[63] Continuation-in-part of Ser. No. 27,565, Mar. 5, 1993, abandoned, which is a continuation of Ser. No. 746,818, Aug. 16, 1991, abandoned.

[51] Int. Cl.$^5$ ............................................. A61B 17/36
[52] U.S. Cl. ........................................ 606/17; 606/7; 606/15
[58] Field of Search ...................... 606/17, 18, 13, 14, 606/15, 16, 7, 6

[56] References Cited

U.S. PATENT DOCUMENTS

| | | |
|---|---|---|
| 4,467,171 | 8/1984 | Ramos . |
| 4,592,353 | 6/1986 | Daikuzono ........................ 606/16 |
| 4,662,368 | 5/1987 | Hussein et al. ..................... 606/7 |
| 4,819,632 | 4/1989 | Davies ............................... 606/17 |
| 4,848,339 | 7/1989 | Rink et al. ....................... 606/16 X |
| 5,093,877 | 3/1992 | Aita et al. ........................ 606/15 X |
| 5,242,438 | 9/1993 | Saadatmanesh et al. ......... 606/17 X |

Primary Examiner—Peter A. Aschenbrenner
Attorney, Agent, or Firm—Dougherty, Hessin, Beavers & Gilbert

[57] ABSTRACT

An operating assembly for use in a liquid operating environment includes a flexible elongated light transmitting fiber having a light reflecting tip mounted thereon for reflecting the light beam laterally. The tip includes a number of features which minimize undesired heating of the tip. The tip is preferably made of solid gold and has a reflecting mirror surface coined on the gold tip. A lateral flushing passageway is disposed through the tip and allows surrounding ambient liquid to flow across the surface of the mirror to aid in cooling the tip and to aid in keeping the mirror clean. The tip is preferably mounted on the fiber by crimping. The tip includes a sufficient volume of material having a sufficient thermal conductivity located between the reflecting mirror and the crimped connection so as to dissipate heat energy which may be generated in the tip and to avoid sufficient heat energy reaching the crimped connection to cause a thermally induced failure of the mechanical attachment of the tip to the fiber at the crimp.

38 Claims, 9 Drawing Sheets

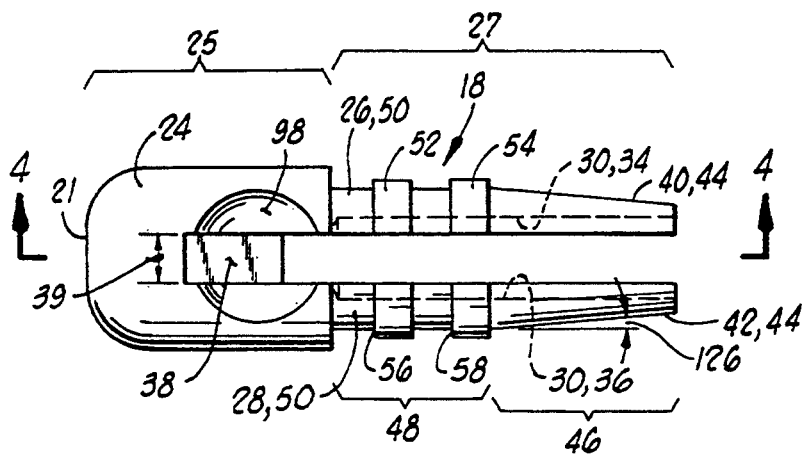
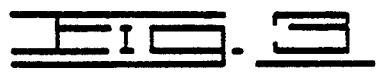
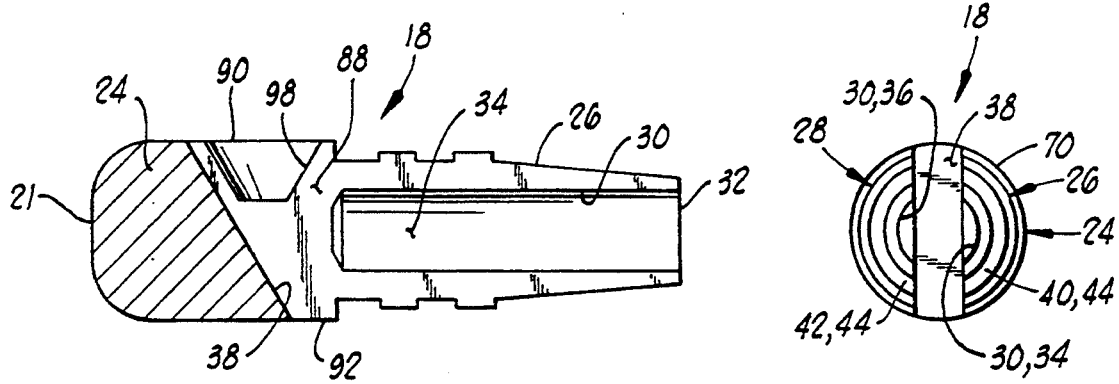
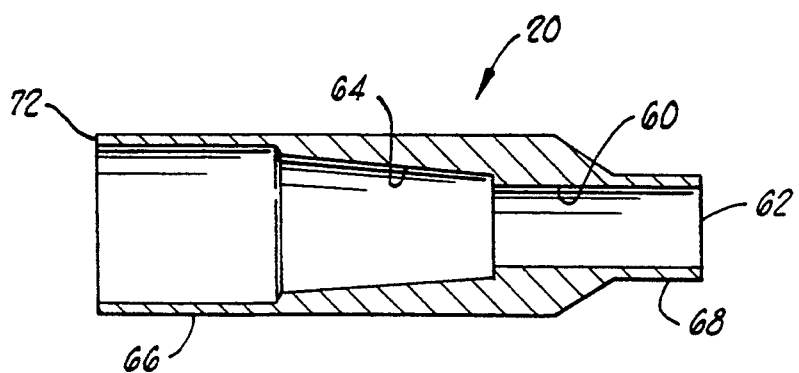
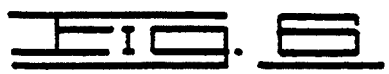

ANGULAR LIGHT INTENSITY DISTRIBUTION OF REPRESENTATIVE BARE AND TIPPED OPTICAL FIBER MEASURED AT 632.8 NM WAVELENGTH.

PERCENTAGE OF TOTAL EMITTED LASER POWER VERSUS INCLUDED ANGLE ($\theta$) FOR REPRESENTATIVE BARE AND TIPPED FIBERS AT 632.8 NM.

5,370,649

LATERALLY REFLECTING TIP FOR LASER TRANSMITTING FIBER

RELATED APPLICATIONS

The present application is a continuation-in-part of patent application Ser. No. 08/027,565 filed Mar. 5 1993, now abandoned, which was a continuation of patent application Ser. No. 07/746,418 filed Aug. 16, 1991, now abandoned.

BACKGROUND OF THE INVENTION

1. Field Of The Invention

The present invention relates generally to devices for use in laterally reflecting light energy from a flexible elongated light transmitting fiber, and more particularly, but not by way of limitation, to such devices designed for use with laser light transmitting fibers.

2. Description Of The Prior Art

One developing area of medical technology involves the application of light energy, typically laser light energy, to a site in the patient's body to alter, remove or destroy tissue in the patient's body. This may be done with bare fibers or with fibers having an optically absorbing metal tip on the distal end. Such tips typically absorb all or part of the laser energy so that the tip itself is heated to a clinically significant extent whereby the tissue is at least partially treated by heat conduction from the heated tip which is placed in contact with the tissue. The tips also may have apertures for directing a portion of the laser light either directly or by reflection upon the tissue to be treated.

Many medical procedures utilizing such tips are more easily accomplished if the laser energy is reflected laterally from the longitudinal axis of the fiber so that it can be directed upon tissue which would be difficult to treat with light emitted axially from the fiber.

SUMMARY OF THE INVENTION

The present invention is directed to a laterally reflecting tip which reflects substantially all incident laser light energy laterally outward through an aperture so that there is no clinically significant heating of the tip. The tip includes an elongated, thin, cylindrical body having a fiber receiving longitudinal opening for receiving the distal end portion of the fiber. The body has a lateral passageway defined diametrically therethrough and intersecting the longitudinal opening. A reflecting mirror surface means is defined on the body for reflecting light from the fiber laterally outward through the lateral passageway. The lateral passageway being disposed diametrically through the body provides a flushing means for permitting surrounding fluid to flow through the lateral passageway across the reflecting mirror surface to reduce collection of contaminants on the reflecting mirror surface and also to aid in cooling the tip.

In another aspect, the reflecting tip of the present invention is designed so that whatever heat is generated at the reflecting mirror surface means will be quickly dissipated into the surrounding liquid environment before that heat energy can cause sufficient heating of the mechanical attachment between the tip and the fiber so as to cause a failure of that mechanical attachment.

Both of these goals are accomplished with an operating assembly for use in a liquid operating environment which includes a fiber and a tip.

The fiber is a flexible, elongated, light transmitting fiber having a distal end portion with a distal fiber end defined thereon. The fiber includes a core, a cladding surrounding said core, and an outer protective jacket surrounding said cladding.

The tip is a light reflecting tip including a body and a reduced diameter, hollow, crimping cylinder extending proximally from the body. The body and the crimping cylinder are preferably integrally constructed although they may be separate components which are attached together.

The body and the crimping cylinder have a body bore defined therein. The distal end portion of the fiber is received in the body bore.

The tip is mechanically attached to the fiber by at least one crimp in the crimping cylinder. This crimp mechanically attaches the tip to the outer protective jacket of the fiber. Preferably, there are a plurality of such crimps.

A reflecting mirror surface means is defined on the body for laterally reflecting light from the fiber. The body has a lateral flushing passageway means defined laterally through the body and intersecting the body bore for permitting surrounding liquid to flow through the lateral flushing passageway means across the reflecting mirror surface means. This flow through the flushing passageway aids in cooling the tip and also aids in keeping the reflecting mirror surface means free of debris which further aids in preventing overheating of the tip. It will be appreciated that as optically absorbing tissue debris collects on the reflecting mirror surface means, it will cause undesired heating of the tip which in turn will cause more debris to be accumulated or burned on the mirror surface, which rapidly escalates into an overheating situation if not controlled.

Problems of thermal degradation at the mechanical attachment between the crimp and the outer protective jacket of the fiber are further reduced by designing the tip so that the body includes sufficient material of sufficient thermal conductivity located between the reflecting mirror surface means and the crimp to sufficiently dissipate to the liquid operating environment the heat generated at the reflecting mirror surface means so that the temperature at the crimp remains sufficiently low that there is no failure of the mechanical attachment of the tip to the outer protective jacket of the fiber during normal operation of the assembly.

Numerous objects, features and advantages of the present invention will be readily apparent to those skilled in the art upon a reading of the following disclosure when taken in conjunction with the accompanying drawings.

BRIEF DESCRIPTION OF THE DRAWINGS

FIG. 3 is a plan view similar to FIG. 1 of the elongated body of the two-piece tip assembly of FIGS. 1 and 2.

FIG. 4 is an elevation sectioned view of the body of FIG. 3 taken along line 4—4.

FIG. 5 is a right end view of the body of FIG. 4.

FIG. 6 is an elevation sectioned view of the sleeve piece of the two-piece tip assembly of FIGS. 1 and 2.

DETAILED DESCRIPTION OF THE PREFERRED EMBODIMENTS

Figure 1:
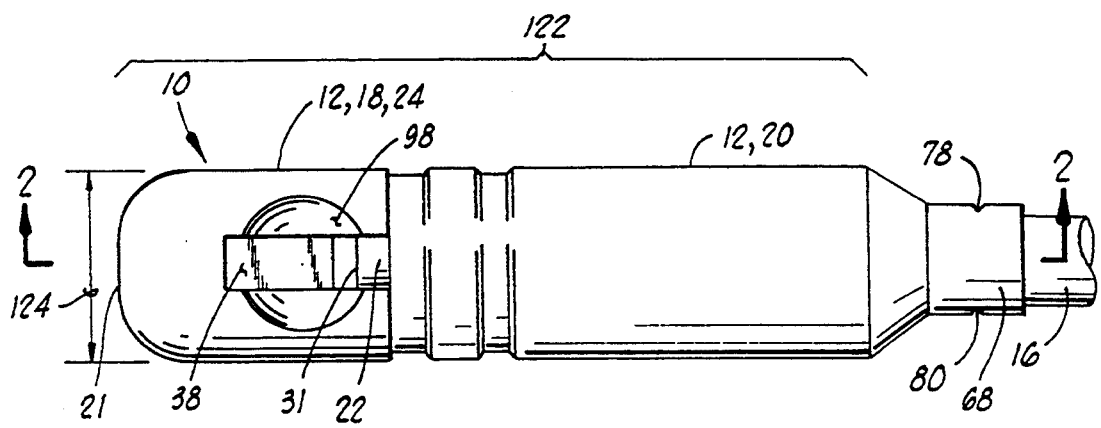
FIG. 1 is a plan view of the light reflecting tip assembled with a flexible elongated light transmitting fiber.
Figure 2:
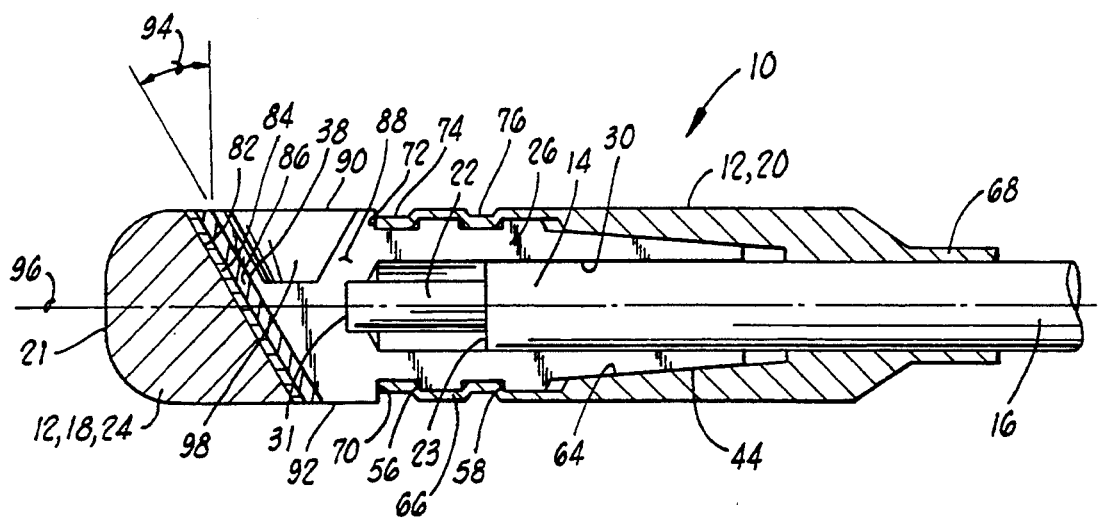
FIG. 2 is an elevation sectioned view taken along line 2—2 of FIG. 1.

Referring now to the drawings, and particularly to FIGS. 1 and 2, a tip and fiber assembly is thereshown and generally designated by the numeral 10. The assembly 10 includes a two-piece light reflecting tip 12 mounted upon a distal end portion 14 of a flexible elongated light transmitting fiber 16.

The two-piece tip 12 includes an elongated body 18 which is best shown in isolation in FIGS. 3-5 and a clamping sleeve 20 which is illustrated in isolation in FIG. 6.

The fiber 16 is a commercially available laser light transmitting fiber. Such fibers include a flexible elongated cylindrical core 22 which is surrounded by a cladding of lower optical refractive index material which is overlain with an outer protective jacket. As seen in FIG. 2, when assembled with the tip of the present invention, the outer cladding and jacket of the fiber 16 are preferably trimmed back to end at 23 with the fiber core 22 extending distally beyond the end 23 of the outer protective layers. This minimizes the possibility of burning of the outer protective layers due to laser energy reflected back from the mirror surface.

The elongated body 18 has a distal head portion 24 and has first and second flexible legs 26 and 28 extending proximally from the head portion 24. Although there is no critical line of distinction between the head portion 24 and the legs 26 and 28, the head portion 24 can generally be described as having a length 25 as seen in FIG. 3, and the legs 26 and 28 can generally be described as having a length 27. Head portion 24 has a squared-off flat end 21.

Figures 10, 11:
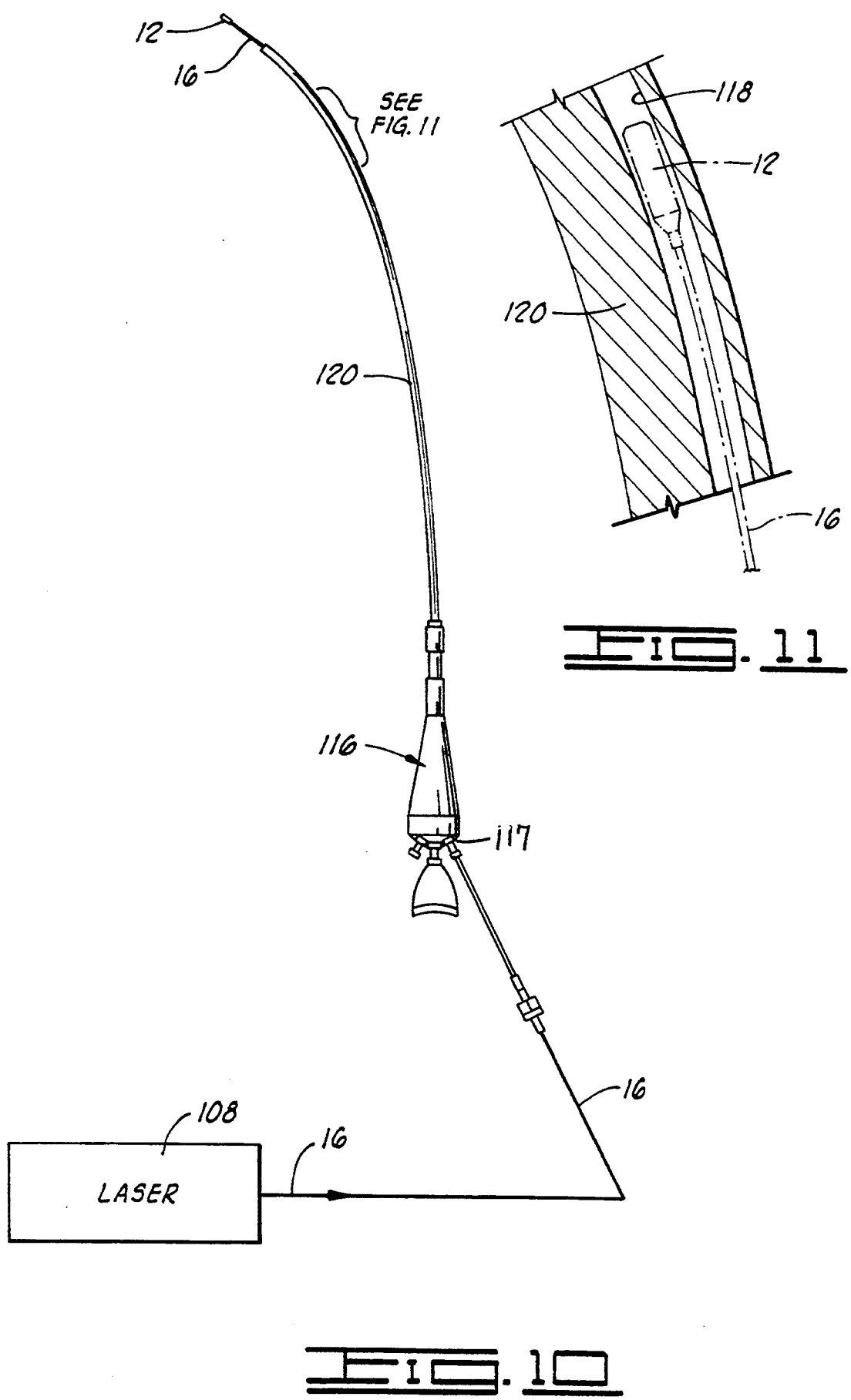
FIG. 10 is a schematic illustration of the laser and endoscope with which the fiber and tip are used.
FIG. 11 is an enlarged sectioned view of a portion of the endoscopic tube of FIG. 10, illustrating the passage of the fiber and tip through a curved endoscopic tube.

As used herein the terms distal and proximal are used in relation to the terminology generally used for the fiber 16 with the distal end of fiber 16 being indicated at 31 in FIG. 2, and with the proximal end of the fiber 16 being the other end which typically would be attached to the laser light source 108 (see FIG. 10). Thus the distal and proximal directions or relative orientations are provided for the tip 12 used in association with the fiber 16.

The clamping sleeve 20 can be more generally described as a clamping means 20 operably associated with the body 18 for urging the legs 26 and 28 radially inward to clamp the distal end portion 14 of fiber 16 therebetween in a manner further described below.

As best seen in FIG. 4, a blind bore 30 is drilled into the proximal end 32 of body 18 thus defining partially cylindrical inner surfaces 34 and 36 on legs 26 and 28, respectively, which surfaces 34 and 36 define a body bore means 30 for closely receiving and clamping the distal end portion 14 of the fiber 16 therebetween.

The body 18 can be described as having a plurality of legs, which in the preferred embodiment are two and only two legs 26 and 28. The head portion 24 has a reflecting mirror surface means 38 defined thereon for reflecting light emitted from the distal end 31 of fiber 16 laterally outward. The body bore means 30 terminates short of the reflecting mirror surface 38.

The legs 26 and 28 have proximal conically tapered outer surface portions 40 and 42, respectively, which collectively define a conically tapered outer body surface 44 extending over a length 46.

A distal portion 48 of legs 26 and 28 defines a generally cylindrical outer surface 50 having first and second annular radially outward extending flanges 52 and 54 each of which has a distally facing shoulder 56 and 58, respectively, defined thereon.

The body 18 is preferably formed from a cylindrical stainless steel blank or other biocompatible material which is machined to have the appearance shown in FIGS. 3 and 4. The lateral passageway 88 and legs 26 and 28 are partially formed by milling a slot having the width 39 as seen in FIG. 3 into the cylindrical blank. As further described below, the body 18 may also be formed of solid gold in which case it will be cast or machined in the shape shown in FIGS. 3 and 4.

The clamping sleeve 20 which is shown in its unassembled state in FIG. 6, is designed to be slidably received about the legs 26 and 28. Clamping sleeve 20 has an axial sleeve bore 60 defined through its proximal end 62 for closely receiving the fiber 16. Clamping sleeve 20 further includes a tapered conical sleeve counterbore 64 complementary to the conically tapered outer body surface 44 so that when the clamping sleeve 20 slides in a distal direction over the legs 26 and 28, engagement of the tapered conical sleeve counterbore 64 with the conically tapered outer body surface 44, causes the legs 26 and 28 to be biased radially inwardly.

The clamping sleeve 20 further includes a thin cylindrical distal portion 66 and a thin cylindrical proximal portion 68 which as further described below are used in securing the two-piece tip assembly together and onto the fiber 16.

As best seen in FIG. 2, a body abutment surface 70, which is an annular shoulder, is defined on the head 24 of body 18. A sleeve abutment surface 72, which is the distal end of sleeve 20, is defined on the clamping sleeve 20 and is arranged to abut the body abutment surface 70 to limit sliding motion of the clamping sleeve 20 over the legs 26 and 28.

The tapered conical sleeve counterbore 64 and the conically tapered outer body surface 44 have an interference fit prior to abutment of the sleeve abutment surface 72 with the body abutment surface 70. Thus, with the fiber 16 in place as shown in FIG. 2, as the clamping sleeve 20 slides distally over the legs 26 and 28, the sliding interference fit between tapered surfaces 64 and 44 causes the legs 26 and 28 to be cammed radially inward thus clamping fiber 16 therebetween.

After the sleeve abutment surface 72 engages the body abutment surface 70, the clamping sleeve 20 is secured to the body 18 by forming first and second circumferentially rolled crimps 74 and 76 in the thin cylindrical distal portion 66 of clamping sleeve 20 so that the crimps 74 and 76 engage the annular shoulders 56 and 58 to prevent the clamping sleeve 20 from sliding backwards off the legs 26 and 28. Additionally, the thin cylindrical proximal portion 68 of clamping sleeve 20 is further secured to the fiber 16 by diametrically opposed staking crimps 78 and 80 as seen in FIG. 1.

Preferably, the lengths of body 18 and clamping sleeve 20 are such that the distance between mirror 38 and the site where legs 26 and 28 clamp the outer cladding of fiber 16 is sufficient to insure adequate thermal transfer to surrounding cooling liquid and prevent overheating of the clamped site.

It will be appreciated that the construction of the legs and clamping sleeve could be reversed so that the sleeve protrudes from the body with the legs being formed on a separate piece which slides into engagement with the sleeve. More generally, the tip 12 can be described as a two-piece tip including a first piece having a plurality of longitudinally extending legs and a second piece including a sleeve slidably received about the legs.

The abutment surfaces 70 and 72 can be more generally described as a limit means 70, 72 for limiting insertion of the legs 26 and 28 within the clamping sleeve 20 and thereby limiting a clamping force applied to the fiber 16 by the legs 26 and 28.

It is noted that the body 18 shown in FIG. 4 differs in one aspect from the body 18 illustrated in FIG. 2, namely in regard to the construction of the reflecting mirror surface means 38.

The reflecting mirror surface means 38 is preferably made of biocompatible 99.9+ percent gold. This can be accomplished in at least two ways. In FIG. 4, the entire body 18 is made from gold and thus all that need be done to complete the reflecting mirror surface means 38 is to treat the surface to make it as smooth and reflective as possible.

FIG. 2, on the other hand, illustrates a construction wherein the major portion of the body 18 is made of a first metal other than gold, preferably 316 stainless steel. An underlying mirror support surface 82 is defined on this first material. Then gold is laid over the underlying support surface in such a way as to form the gold reflecting mirror surface means 38. One preferred manner of doing this is to sputter deposit an underlying gold layer 84 onto the underlying mirror support surface 82, and then to diffusion bond a gold sheet 86 to the underlying gold layer 84.

The diffusion bonded gold sheet 86 preferably is formed from rectangular gold wire having a thickness of at least 0.014 inches thus providing a gold layer thick enough to prevent the chemical action of the surrounding saline medium from corroding completely through the gold layer during typical medical treatment procedures. The gold sheet has a width approximately equal to the width 39 of mirror surface 38.

Regardless of whether the solid gold body of FIG. 4 or the stainless steel body with overlying gold layers of FIG. 2 is used, the final treatment of the gold reflecting mirror surface means 38 is preferably formed by coining the surface. Coining is a mechanical process whereby a very hard, smooth member is pressed against the surface 38 to stamp it or coin it so that it too carries a smooth highly reflective impression.

As is further described below, the smooth, coined, gold reflecting mirror surface means 38 provides a means for reflecting substantially all of the light energy incident thereon from the fiber 16.

Alternatively, the mirror surface 38 could be made smooth by electro or mechanical polishing or by chemical etching.

In designing a tip for maximum reflection so that substantially all laser light energy incident upon the reflecting surface 38 is reflected, it is necessary to choose the reflecting material dependent upon the particular laser being utilized. Different reflective materials have more efficient reflective characteristics for different wavelengths of laser light. For example, when utilizing an Nd:YAG laser having a characteristic wavelength of 1064 or 1318 nanometers; a Ho:YAG laser having a characteristic wavelength of 2100 nanometers; a semiconducting diode laser operating at 805 nanometers; a dye laser operating in the 630-800 nanometer range; an Alexandrite laser having a 680-800 nanometer tuning range; or a Sapphire laser having a 680-800 nanometer tuning range, the reflective surface 38 is preferably made of gold.

On the other hand, for a frequency doubled Nd:YAG laser having characteristic wavelengths of 532 or 659 nanometers, a platinum surface 38 is preferred. Similarly, the platinum surface is preferred for an Argon Ion laser emitting radiation with wavelengths in the 428-528 nanometer range, and for a dye laser having a 400-630 nanometer tuning range.

Gold and platinum are chosen as preferred mirror surfaces on the basis of their high optical reflectivities and their relative stabilities in a warm aqueous saline solution environment.

As is best seen in FIG. 2, the body 18 has a lateral passageway 88 defined diametrically therethrough which intersects the body bore means 30. The lateral passageway 88 has diametrically opposite first and second end openings 90 and 92, respectively. The lateral passageway 88 extends across and runs parallel to the reflecting mirror surface means 38, and thus due to the slope of the reflecting mirror surface means 38, the second end opening 92 is substantially smaller than the first end opening 90 of lateral passageway 88.

The reflecting mirror surface means 38 is set at an angle 94 to the longitudinal axis 96 of the fiber 16 and tip 12. Thus light exiting the distal end 31 of fiber core 22 falls axially (with a small divergence) onto the reflecting mirror surface means 38 and then is reflected laterally out the larger first end opening 90 of lateral passageway 88.

There is some angular diffusion of the light which reflects from the reflecting mirror surface means 38 so that it tends to diffuse into a conical beam, and the body 38 has a conical cavity 98 superimposed upon the larger first end opening 90 of lateral passageway 88 thus permitting the reflected beam to pass laterally outward without impinging upon any other portions of the tip 12 other than the reflecting mirror surface means 38.

The tip 12 is constructed for usage in any number of medical procedures wherein the tip is used to direct laser light onto human tissue to treat the same. The tip 12 is typically immersed in an aqueous saline solution during operation, but it will be appreciated that often the solution is contaminated with proteins from the surrounding body tissue. If these proteins are allowed to build up on the reflecting mirror surface means 38, it of course will significantly degrade the operation of the tip 12. The lateral passageway 88 extending completely laterally through the body 18 over the reflecting mirror surface means 38 provides a flushing means 88 for permitting surrounding fluid, typically saline solution, to flow in one of the first and second end openings 90 and 92, then across the reflecting mirror surface means 38, then out the other of the first and second end openings, thus tending to cleanse the reflecting mirror surface means 38 and to reduce collection of contaminants on the reflecting mirror surface means 38.

The flushing of saline solution through the lateral passageway 88 also aids in carrying away saline solution heated by laser light passing therethrough to prevent any significant heat buildup adjacent the tip 12. As further shown below, the tip 12 is designed for substantially complete reflection of the laser light energy incident upon mirror 38. There is no clinically significant heating of tip 12.

Figure 7:
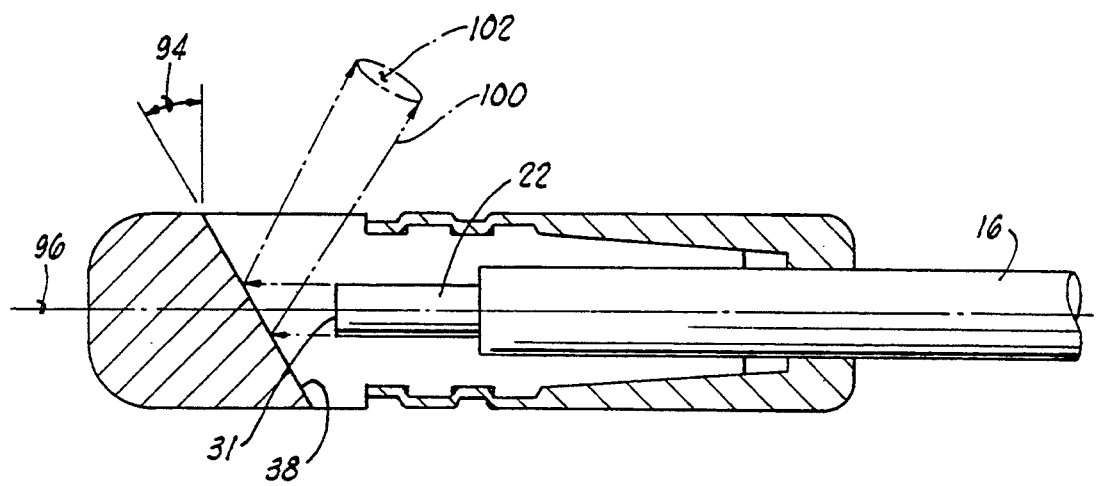
FIG. 7 is a schematic illustration similar to FIG. 2 showing the beam spread of a beam reflected from a flat mirror.
Figure 8:
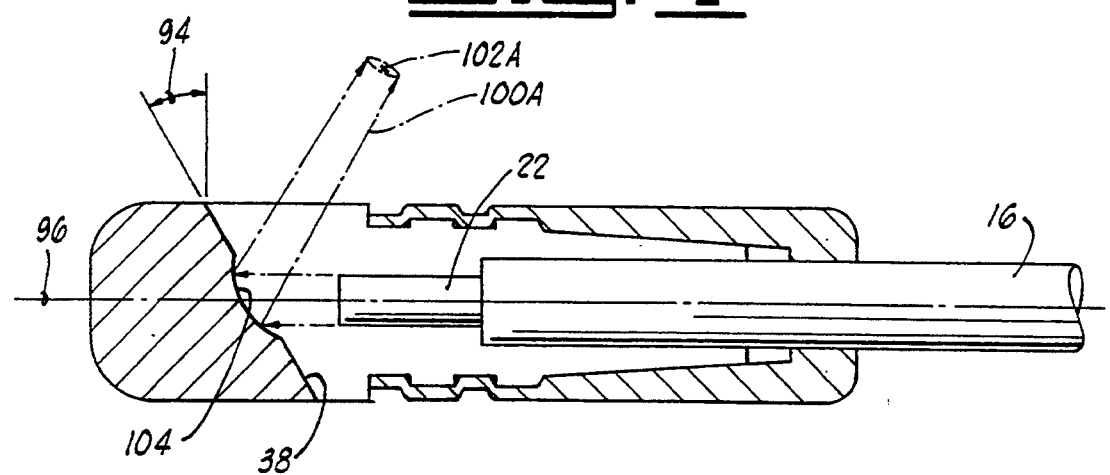
FIG. 8 is a view similar to FIG. 7 showing the beam spread of a beam reflected from a concave mirror.
Figure 9:
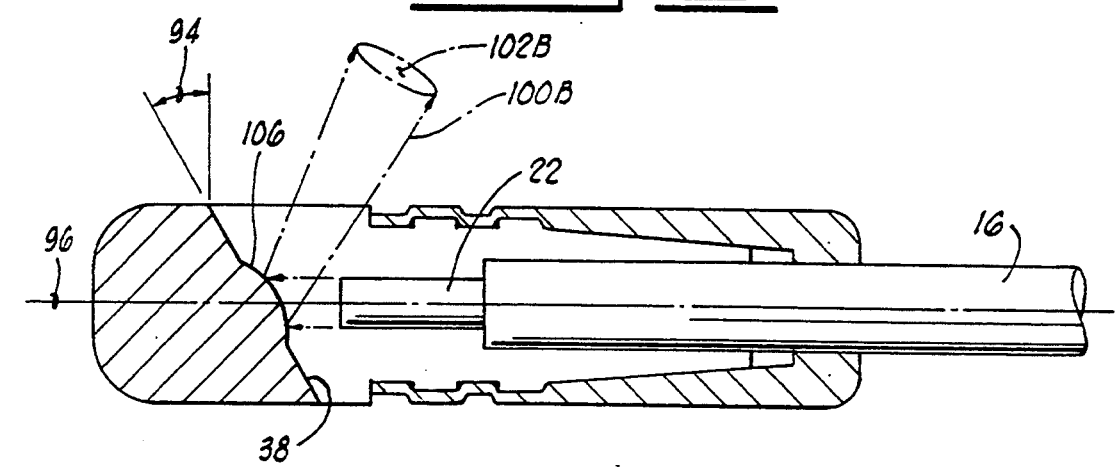
FIG. 9 is a view similar to FIG. 7 showing the beam spread of a beam reflected from a convex mirror.

FIGS. 7-9 are somewhat simplified versions of FIG. 2 and they illustrate various modifications that can be made to the reflecting mirror surface means 38.

FIG. 7 illustrates the flat planar reflecting mirror surface means 38 previously described with regard to FIGS. 2 and 4. In a preferred embodiment the angle 94 of surface 38 is $37\frac{1}{2}°$, and the distal end 31 of fiber core 22 is cut square, i.e., it defines a plane normal to the axis 96 of the fiber. With such an arrangement, and with a highly reflective coined gold reflecting mirror surface means 38, the reflected beam 100, the outer extremities of which are shown in phantom lines will diverge slightly from a cylindrical beam due to divergence upon exiting fiber core 22 and due to imperfect reflection of the mirrored surface 38 so as to form a reflected light spot 102. In a preferred embodiment the flat coined gold reflecting mirror surface means 38 of FIG. 7 is a means for providing a generally circular reflected light spot size 102 no greater than 3 mm diameter at a distance of 1.05 cm along the central ray of the deflected beam from the central axis 96 of the fiber 16.

It is noted that with the specified angle 94, the reflected beam will reflect somewhat in a proximal direction. This back reflection is a significant aid in directing the reflected beam to hard-to-reach portions of cavities within the human body. The angle of reflection of the beam can of course be modified as desired by modifying the angle 94 and the configuration of the reflecting surface 38. Also, the distal end 31 of the fiber core 22 can be cut at an angle which will also affect the dispersion and direction of the light beam emitted therefrom.

As best seen in FIG. 2, there is an axial clearance between the distal end 31 of fiber core 32 and the reflecting mirror surface means 38. This permits the lowermost reflected beam to exit through the lateral passageway 88 without impinging upon the fiber end 31 or any portion of the tip 12 other than the mirror 38.

Depending upon the type of treatment being conducted, it may be desirable for the reflected light spot 102 to be either more diffused or more concentrated. This can be accomplished by modifying the reflecting mirror surface means 38 as shown in FIGS. 8 or 9 to concentrate or disperse the beam, respectively.

In FIG. 8, the reflecting mirror surface means 38 has a concave portion 104 which is impinged by the beam from fiber core 22 thus concentrating the reflected beam 100A to form a smaller reflected beam spot 102A as compared to FIG. 7.

In FIG. 9, the reflecting mirror surface means 38 includes a convex portion 106 which causes the reflected beam 100B to be more dispersed and thus form a larger reflected beam spot 102B as compared to the apparatus of FIG. 7.

It will be appreciated that FIGS. 7-9 are only schematically illustrated and are not necessarily geometrically correct. The angles of the beams have been somewhat exaggerated to illustrate the difference between the various embodiments.

FIG. 10 schematically illustrates the various apparatus with which the fiber 16 and tip 12 are typically used. The proximal end of the fiber 16 is connected to a laser 108 which produces the laser light which is transmitted through the fiber 16 and then reflected by tip 12. In the present disclosure the word light is used in its broad sense, meaning electromagnetic radiation which propagates through space and includes not only visible light, but also infrared, ultraviolet and microwave radiation. In the preferred embodiment, the light transmitted by fiber 16 is laser light produced by the laser 108.

The fiber 16 is typically utilized with a conventional endoscope 116, which may be rigid or flexible, and which carries the fiber 16 in a cylindrical passage 118 defined in an endoscopic tube 120. The endoscopic tube 120 may include a parallel optical viewing fiber (not shown) and parallel fluid flow conduits (not shown). Also, the cylindrical passage 118 may itself be utilized as a fluid flow passage to allow irrigating fluids to flow to the tip 12.

It will be appreciated that depending upon the medical procedure being performed, the endoscopic tube typically may need to pass through various curved cavities in the human body so as to reach the area to be treated. In such case a flexible endoscope will be used.

The tip 12 and fiber 16 which are assembled according to the present invention preferably are constructed so that they can pass through the cylindrical passage 118 of endoscopic tube 120 when the endoscopic tube 120 is contorted in the necessary fashion. Thus, the fiber 16 assembled with tip 12 must be capable of curving to pass through the curved cylindrical passage 118. Also, the fiber 16 and tip 12 must pass through the endoscope 116 itself. Typically the most severe curvature through which the fiber 16 and tip 12 must pass is the bend at connection 117 where the fiber 16 enters the endoscope 116 from a laterally offset position and then must pass into the tube 120. The radius of curvature of this bend on existing endoscopes is approximately 10 cm. This passage may have a diameter on existing endoscopes as small as 2.5 mm.

FIG. 11 is a schematic, segmented, cross-section portion of the endoscopic tube 120 in the curved area designated in FIG. 10. The fiber 16 and tip 12 are shown in phantom lines in FIG. 11 as they would appear when the tip 12 and fiber 16 are being run in a distal direction through the passage 118 so that they ultimately will extend from the distal end of endoscopic tube 120 as illustrated in FIG. 10.

A typical passage 118 of available endoscopic tubes 120 has a diameter of no greater than 2.5 mm. The preferred optical fiber described below has a design minimum bending radius of 1 cm which can easily conform to passage 118 so long as the tip 112 can fit through the curved passage. Since the most severe bend to be encountered is that at junction 117, the fiber 16 and tip 12 should be so constructed and dimensioned as to provide an assembly capable of passing through a curved cylindrical passage having a diameter of 2.5 mm and a radius of curvature of 10 cm.

Prior art tip constructions for laterally reflecting tips have been relatively bulky and have been incapable of passing through such a narrow curved passage. The present invention has solved this problem. In a preferred embodiment this is accomplished by constructing the tip 12 to have a length 122 (see FIG. 1) of 0.3543 inches (9,000 mm) and an outside diameter 124 of 0.0866 inches (2,200 mm). This tip is generally cylindrical in shape and is concentrically mounted upon the distal end portion 14 of fiber 16. Preferably the tip 12 has a maximum diameter 124 of no greater than 2.2 mm, and a length no greater than 1 cm.

The preferred light transmitting fiber 16 for use with the tip 12 having the dimensions just described is a conventional fused silica fiber. This fiber has a minimum bending radius of 1 cm. The silica core has a diameter of 600 microns and the fiber with cladding has an outside diameter of 0.040 inch which is clamped within the bore 30 of tip 12 which has a bore diameter of 0.040 inches.

In this preferred embodiment the tapered outer surface 44 and tapered inner counterbore 64 have an angle of taper such as indicated at 126 in FIG. 3 in the range of from 4.2° to 4.8°.

EFFICIENCY OF REFLECTION

Measurements of reflective optical power and intensity distribution over the reflected beam were made on a group of nine fibers having tips 12 with 99.9% gold reflective surface formed as described above with regard to FIG. 2. Similar measurements were also made on a corresponding group of bare fibers of identical manufacture.

Specifically, measurements were made to assess and compare the reproducibility of values of reflected and emitted power and radiated intensity distribution within each group of optical fibers and to compare the efficiency of the reflection by the actual gold surface relative to the theoretically predicted value for an ideal gold surface.

Figure 12A:
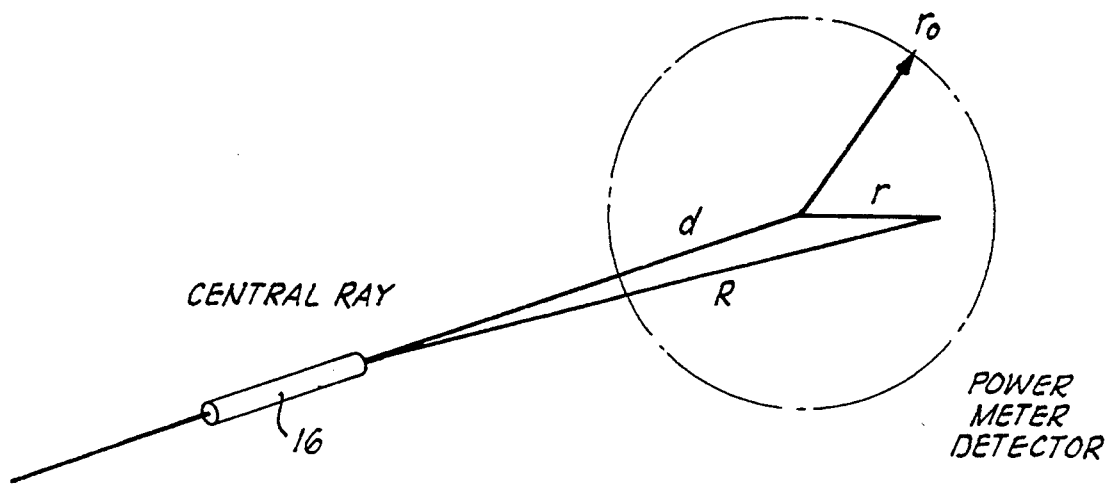
FIGS. 12A and B and 13A and B schematically represent certain tests which were run to determine reflective efficiency of the tips.
Figure 12B:
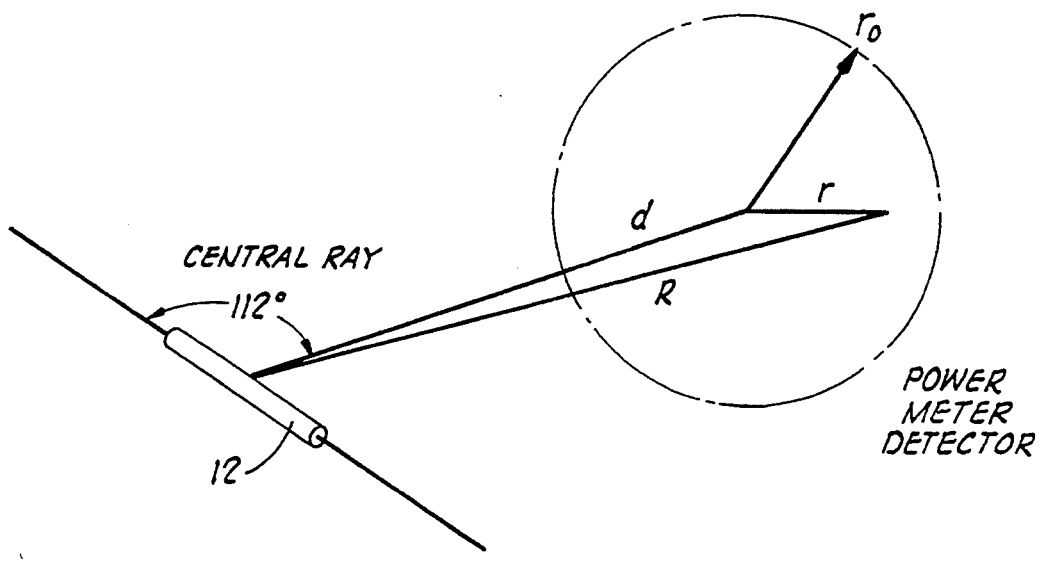

Measurements to determine emitted and reflected radiation power were made using the set-up shown in FIGS. 12A and 12B. In the tip measurements the central ray of the reflected beam was deviated 112 degrees from the parent fiber axis, and impacted the circular detector surface at its center. The central ray of the emerging beam was aligned in similar fashion relative to the detector for measurements on bare fibers.

Measurements to determine the uniformity of reflected power from tipped fibers and of emitted power from the bare fibers respectively, were made at constant input using the Nd:YAG laser power settings of 5, 10 and 20 watts. The distance from either reflecting or emitting surface was kept at 7 centimeters. This was done to keep the fixed geometry for measurement at all power levels selected without bleaching or burning the blackened detector surface.

Experiments were also performed on three fibers randomly picked from the tipped fiber population in order to assess the efficiency or percentage of power reflected in comparison to the average emitted power of the bare fiber population. These measurements were made at 10 watts input Nd:YAG laser power delivered to each fiber and with the fiber end located 1 centimeter from the detector surface so as to collect sensibly all the reflected beam pattern. Collection of the entire beam with this geometry was established from the accompanying measurements (described below) of radiation intensity over the reflected beam.

Figure 13A:
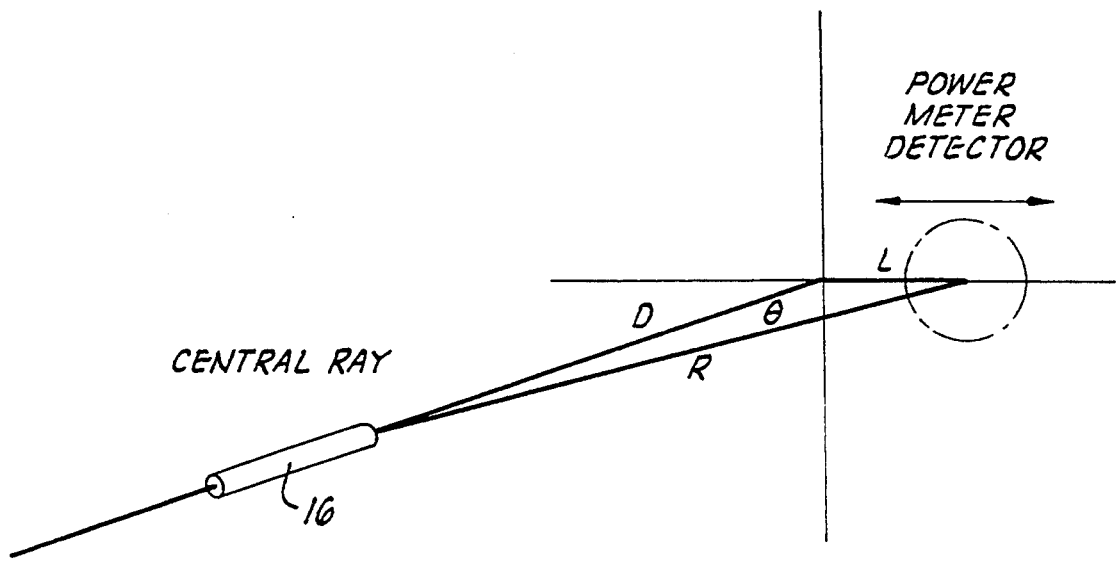
Figure 13B:
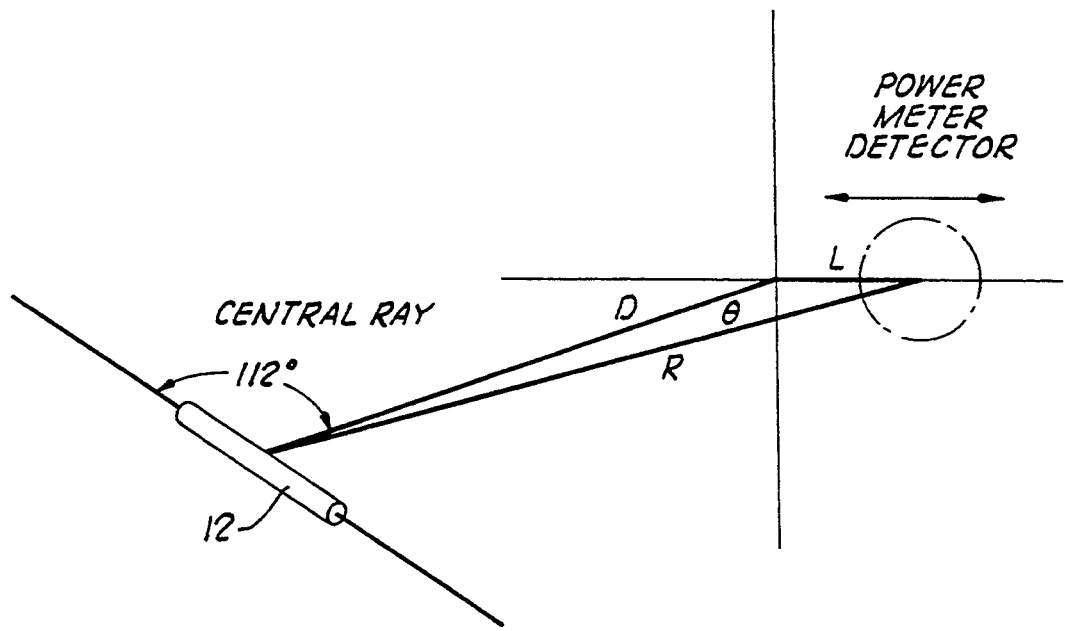

Measurements of the uniformity of distribution of radiation intensity over the cross section of the reflected and emitted beam profiles were made on tipped and bare fibers (two in each population) using the set-up of FIGS. 13A and 13B. Light from a 5-milliwatt helium neon laser (632.8 nanometers) was used.

A Coherent Radiation, Inc. Model 210 laser power meter and detector (25 mm aperture) was used for all measurements of the Nd:YAG laser beam power emitted from either the bare or the tipped fibers. A United Detector Technologies silicon diode based 81 optometer detector was used to measure the angular distribution of the emitted helium neon beam (632.8 nanometers) for each fiber type.

Measurements of laser power emitted by groups of nine each bare and tipped fibers were made under identical conditions of 5, 10 and 20 watts input Nd:YAG laser power. A seven centimeter distance between fiber end or tip and detector was maintained for all measurements. Values of average power and standard deviation for both bare and tipped fibers for the three different input Nd:YAG laser powers are found in the following Table 1.

TABLE 1

Measured Nd:YAG Laser Power Values From Bare and Tipped Fibers

| Laser Power Settings (w) | Bare Fiber (w) | Tipped Fiber (w) | Distance (cm) |
|---|---|---|---|
| 5 | 4.62 ± 0.29[a,b] | 3.36 ± 0.15[b] | 7 |
| 10 | 9.62 ± 0.34[b] | 7.06 ± 0.48[b] | 7 |
| 20 | 18.17 ± 0.68[b] | 13.29 ± 0.82[b] | 7 |
| 10 | 9.72 ± 0.32[c] | 8.81 ± 0.21[c] | 1 |

[a]Numbers are average ± standard deviation
[b]n = 9
[c]n = 3

As seen in Table 1 the bare fibers on the average emitted 92, 96 and 91 percent of the input laser power at 5, 10 and 20 watts. This clustering suggests reproducible light transmission by the parent fiber family.

Results for the nine tipped fibers in Table 1 show the strong uniformity of the percentage of reflected laser power. At laser input power values at 5, 10 and 20 watts, respectively, detected power values from the tipped fibers were nominally 73 percent (see Table 1) of the average power emitted from the bare tip of the parent fiber at each value of input laser power. This large difference arises from the reflected beam diameter exceeding the detector aperture diameter at the 7 cm. detector to tip distance: thus only a fraction of the total reflected power was measured.

In a subsequent experiment, the distance between the detector surface and the tip 12 was decreased to one centimeter. The detected average value of power emitted at 10 watts of laser input from three tipped fibers was 8.8 plus or minus 0.21 watts. Light distribution analysis described below ensured that at this one centimeter detector to reflecting tip surface distance that essentially 100 percent of the reflected light was collected by the detector. Relative to the average emitted power of the bare fiber family (9.72 plus or minus 0.32 watts) at 10 watts input the tipped fiber emits approximately 92 plus percent of the power emitted by the bare tip onto the gold reflecting surface. Allowing for about 98 percent theoretical reflectivity of the pure gold surface and the possibility of two or more multiple reflections from the roughness of a real production gold surface and the non-zero standard deviations associated with the experimentally determined average values of power emitted by both bare and tipped fibers, actual differences between bare fiber and reflected power values can be considered to be negligibly small and the bare fiber and tipped fibers can be considered to emit essentially equal power values at equal Nd:YAG laser input values.

Figure 14:
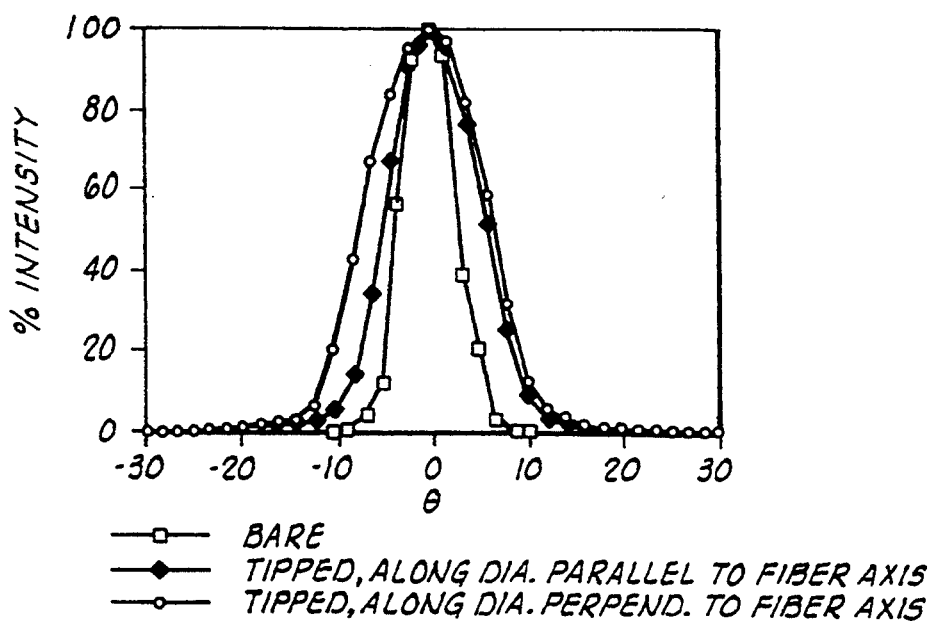
FIGS. 14 and 15 are graphic representations of the spreading of the light beam energy by a flat reflective mirror surface.

Light distributions from He-Ne neon laser light (632.8 nm.) were determined for representative bare fiber and tipped fibers (two types each). The average distributions are shown in FIG. 14. Examination of these figures shows a spread of the beam from the bare fiber upon reflection in the tip 12. This undoubtedly arises from a small diffuse scattering component due to surface irregularities on the real gold surface. This scattering spreads the beam from the tip 12 in essentially symmetrical fashion about the central ray. The significant effect of reflection of the beam from the fiber end 31 is one of widening without introduction of relatively more or less intense regions of light that is hot or cold spots within the bell-shaped light pattern emitted by the bare tip fiber. Therefore, the shape of the bare fiber beam and that of the reflected side directed beam from tip 12 are essentially equivalent.

Figure 15:
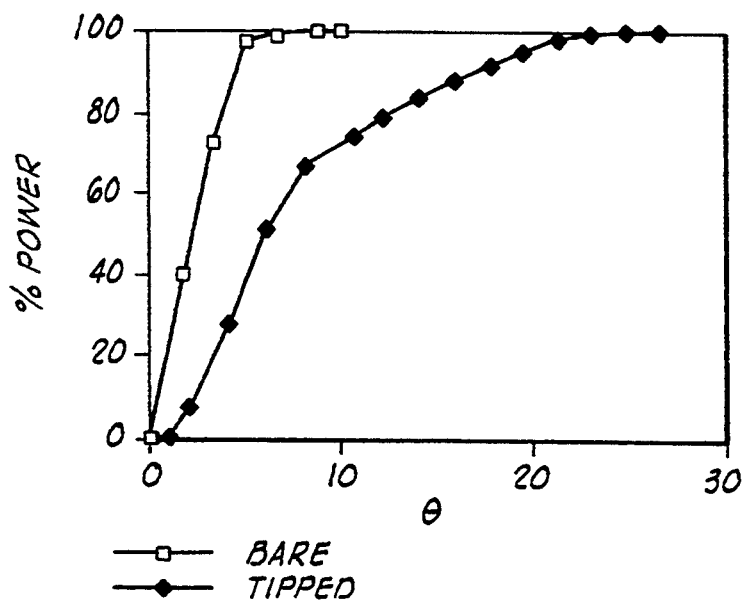

Integration of the light flux emitted by both fiber tips over the detector aperture gives the total power incident upon the detector. The flux integral P is given by:

$$P = \frac{2}{DZ} P_0 \int_0^{r_0} F(\theta) \cos^4\theta\, r\, dr$$

where $P_0$ is the total light power emitted by the tips, $F(\theta)$ is the angular variation in the light intensity, and r is the radial distance on the surface of the detector of aperture radius $r_0$. The geometry is shown in FIGS. 12A and 12B. Percentage values of the integral for various detector apertures are shown in FIG. 15 for both bare and tipped fibers. Performance of the integration for the tipped fiber placed 7 and 1 centimeters, respectively, away from the detector surface gives $P=0.717$ and $1.0\times$the emitted power, respectively. These values are consistent with average values measured at distances of 7 and 1 cm. of, respectively, 0.73 and $0.91\times$the average power emitted by the bare fiber upon the reflecting surface 38 of tip 12. Since light back scattering decreases as wavelength increases relative to scatterer sizes going about as one divided by wavelength raised to the nth power (n typically between 1 and 4), the width of the light distribution at the 1.06 micron Nd:YAG wavelength reflected from the tip 12 is expected to be slightly smaller than the measured distribution at 632.8 nanometers.

Values of the fraction of total laser power contained within the beam as angle increases (radial distance increases) are plotted in FIG. 15 for both the bare and tipped fibers. Use of these plots shows that (1 minus exp(−2)) of the total power within the beam from the bare fiber end and the tip 12 is contained within 5 and 16 degrees, respectively, of the central ray of the light distribution. As the result of the wider nature of beam from tip 12 equal spot sizes of radius R. tissue are achieved with the respective bare and tipped fibers held at different distances D. from the tissue surface. For various spot sizes R. in the range of 1 to 4 millimeters, the associated values of the distance to tissue are tabulated in the following Table 2.

TABLE 2

Spot Size and Distance Values for Bare and Tipped Fibers

| $R_0$ (mm) | $\theta_0$ (deg) | D (cm) | Fiber Type |
|---|---|---|---|
| 1 | 5 | 1.14 | Bare |
| 1 | 16 | 0.35 | Tipped |
| 2 | 5 | 2.28 | Bare |
| 2 | 16 | 0.70 | Tipped |
| 4 | 5 | 4.56 | Bare |
| 4 | 16 | 1.40 | Tipped |

$\tan \theta_0 = R_0/D_0$

The results of optical property assessments on the tip 12 and the bare fibers allow the following essential equivalences to be identified:

(1) Output beams of both tips are centrosymmetric with respect to the central ray of peak intensity with uniform gradual fall off in intensity with radius in all directions. Essentially no random hot or cold spots are present.

(2) The tip 12 reflects essentially all (92±4%) incident laser beam energy. Power densities at tissue equal to that of equivalent bare fiber can be achieved with the use of tip 12 by adjusting the tip to tissue distance, thus adjusting spot size.

(3) The essential action of the tip 12 is to reflect the laser beam laterally.

The substantially complete reflectivity of the gold mirror surface 38 also means that there is no clinically significant heating of the tip 12 itself, i.e., the tip 12 does not become sufficiently hot to significantly affect the tissue being treated if the tip 12 is placed in contact with the tissue but is oriented so that the reflected light beam does not fall upon the tissue contacted by the tip. This is shown by the following example.

EXAMPLE NO. 1

Figure 16:
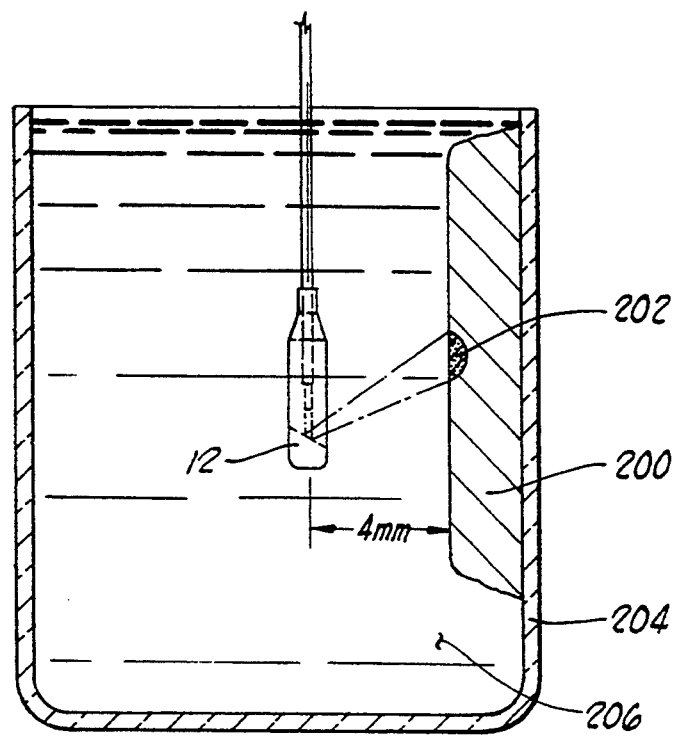
FIGS. 16 and 17 schematically illustrate the methodology of an example test which shows that there is no clinically significant heating of the tip.
Figure 17:
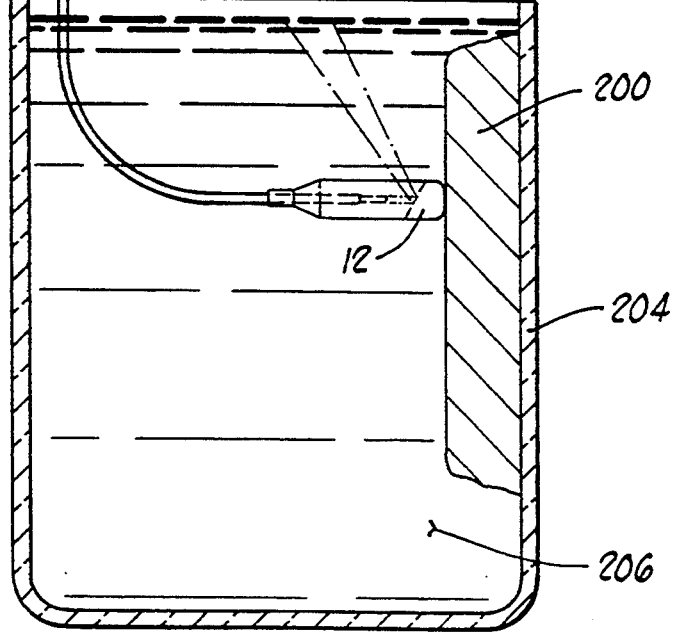

The depths of coagulation achieved by using the tip 12 as a contact heating probe (no direct irradiation) and by directly irradiating tissue (no direct contact) were compared using 60 W of Nd:YAG laser power. Bovine liver (*in vitro*) was used as the test tissue. The arrangement for each experiment with the tip 12 is shown in FIGS. 16 and 17. The distance of tip 12 from the tissue is 4 mm in FIG. 16 which gives a spot size approximately equal to the 2.2 mm diameter contact size in FIG. 17. In FIG. 6 the tip 12 is immersed in water 206 in a beaker 204. The test tissue 200 is placed against one side of the beaker.

After exposure for one minute with 60 W laser input power, surface bleaching of the liver color was noted at both the contact and irradiated sites. In FIG. 16 the bleached spot is indicated at 202. Perpendicular sections cut with a scalpel through each bleached spot disclosed coagulation bleaching to extend to depth of approximately 700 micron (0.7 mm) and 7 mm at the contacted and irradiated sites, respectively. Thus, direct exposure to the laser beam as opposed to only heating the tip (in contact only with tissue) with the beam resulted in a 10-fold deeper coagulation depth and a 10-fold greater coagulation efficiency at equal exposure times.

Figure 18:
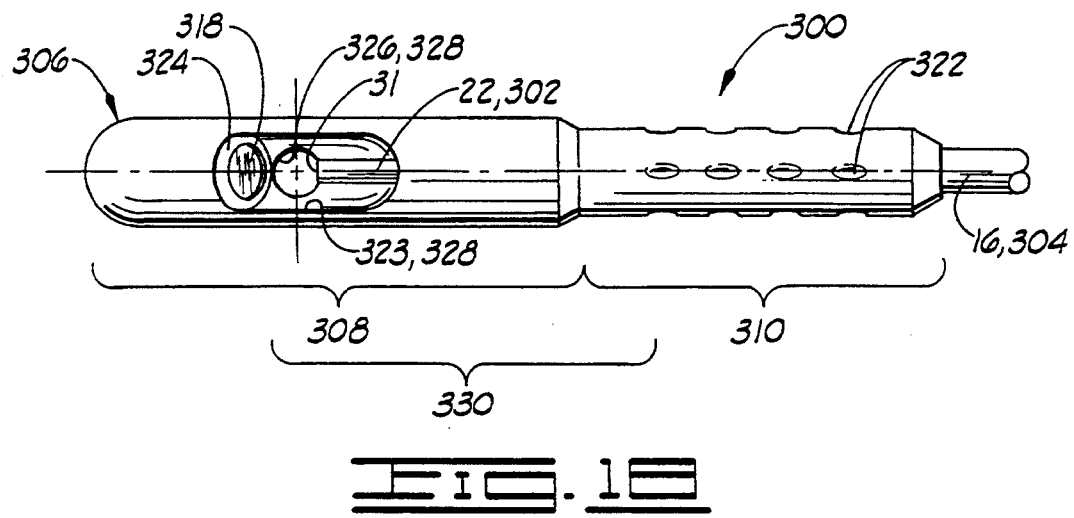
FIG. 18 is a plan view of another embodiment of the present invention having a single piece tip.
Figure 19:
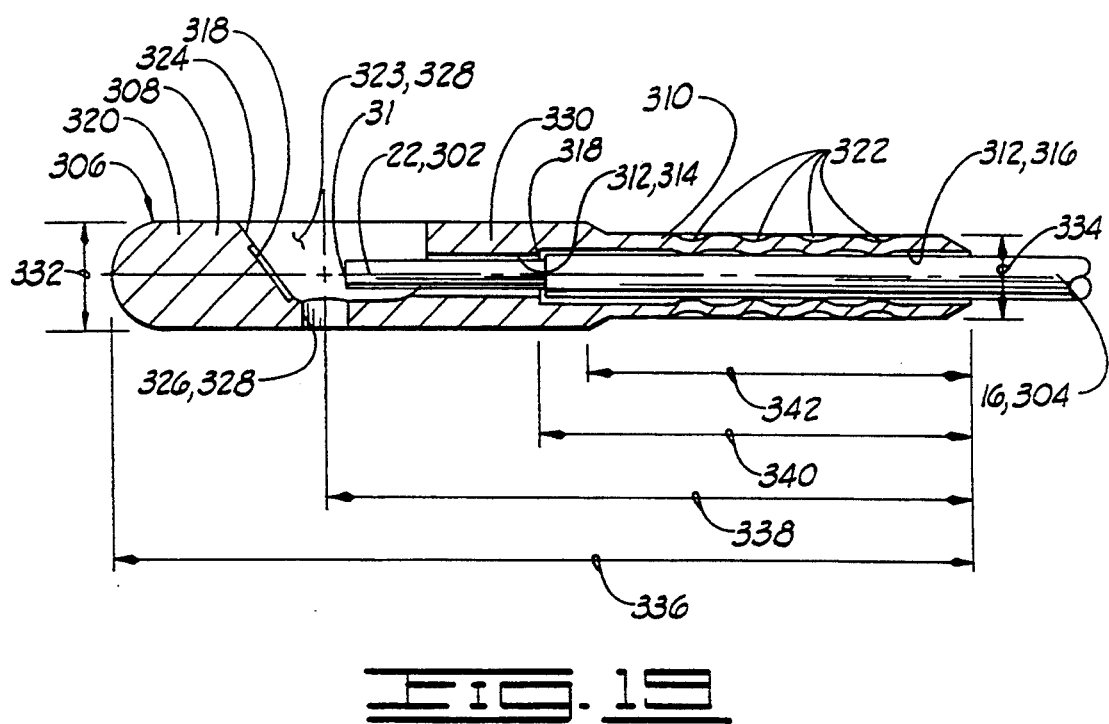
FIG. 19 is a sectioned view taken along line 19—19 of FIG. 18.

The Embodiment of FIGS. 18 and 19

FIGS. 18 and 19 illustrate an alternative embodiment of an operating assembly generally designated by the numeral 300. The assembly 300 includes the flexible elongated light transmitting fiber 16 having the distal end portion 22 with the distal fiber end 31 defined thereon. As previously described above, the fiber 16 includes a quartz core, a cladding 302 surrounding the core, and an outer protective jacket 304 surrounding the cladding. The outer protective jacket 304 has been stripped back from the distal end portion 22 so that the cladding 302 is exposed. The outer protective jacket which is designated by the numeral 304 is also seen in FIGS. 18 and 19. The cladding 302 is an optical mirror formed of a silica ceramic polymer. The outer protective jacket is typically formed of Teflon ® brand polytetrafluroethane.

The operating assembly 300 includes the fiber 16 and a light reflecting tip generally designated by the numeral 306. The tip 306 includes a body 308 and a reduced diameter hollow crimping cylinder 310 extending proximally from the body 308. In the embodiment of FIGS. 18 and 19, the body 308 and crimping cylinder 310 are integrally constructed from a single piece of material. Preferably, the body 308 and crimping cylinder 310 are machined from a piece of 24-carat gold material having in excess of 99.9% purity.

As seen in FIG. 19, the body 308 and crimping cylinder 310 have a body bore 312 defined therein having a main bore portion 314 and a counterbore portion 316. The distal end portion 22 of the fiber 16 is received in the body bore 312. The junction between the main bore portion 314 and counterbore 316 defines a ledge 318 which abuts a distal end of the outer protective jacket 304. This aids in positioning the distal end 31 of fiber 16 at the appropriate distance from the reflecting mirror surface means 318 which is formed on a distal head portion 320 of the body 308. The reflecting mirror surface 318 is preferably formed by coining.

The tip 306 is attached to the fiber 16 by a plurality of crimps 322 formed in the crimping cylinder 310 to crimp the cylinder 310 tightly against the outer protective jacket 304 of fiber 16 so as to mechanically attach the tip 306 to the fiber 16. The tip 306 is attached to the fiber 16 solely by the plurality of crimps 322. Tip 306 is free from attachment to any structure other than fiber 16.

The body 308 has an oval-shaped concavity 323 defined therein which intersects the body bore 312. The concavity 323 includes a flat surface 324 which has the reflecting mirror surface means 318 formed therein. A radial bore 326 is defined in the other side of body 308 and intersects the concavity 323. Concavity 323 and radial port 326 collectively define a lateral flushing passageway 328 intersecting the body bore 312. The lateral flushing passageway 328 permits surrounding liquid to flow therethrough across the reflecting mirror surface means 318 thereby aiding .in cooling the tip 306. The lateral flushing passageway 328 has liquid from the surrounding liquid environment flowing in one end thereof, typically in through the radial port 328 and out the other end thereof, typically through the open side of concavity 323. The laser energy passing through the liquid in the space between the distal end 31 of fiber 16 and the reflecting mirror surface 318 tends to cause boiling of that liquid. Gaseous bubbles from this boiling move away from the tip out through the open end of concavity 323 thus tending to draw surrounding ambient liquid into the radial port 326 by a Venturi effect. The transverse flushing passageway supplies to mirror and fiber tip a vigorously flowing fluid stream drawn from the surrounding fluid within the patient's body cavity through the flushing passageway by the Venturi effect. This effect is initiated by the escaping flow of fluid heated both by absorption of the laser beam and by conduction from the laser heated mirror surface. Laser power is typically high with the present invention, up to 80 watts. Thus, the flow rate is large and turbulent. This is evidenced by visualization of rapidly swirling water region of different heat dependent optical refractive index as seen in nearly boiling water heated in a pan. The effect is to cool and flush the metal mirror surface and body.

The lateral flushing passageway 328 is free from communication with any source of flushing fluid other than this surrounding liquid from the surrounding liquid environment; this is contrasted to certain prior art designs wherein flushing fluid is force fed through the tip bore 312 and out through a lateral opening in the tip.

The primary mode of failure encountered by metal tipped laser fibers tends to be the failure of the mechanical attachment of the tip to the fiber. This typically will occur when excessive heating of the tip occurs thus causing thermal degradation of the outer protective jacket 304 to which the tip is attached. We have discovered that in normal operating conditions, such failures can be avoided through a combination of several design features, all of which contribute to reducing this undesired heating of the tip. The first such feature is the use of a highly reflective coined gold mirror surface 318 which reflects substantially all of the light incident thereon. This is contrasted to many prior art designs which intentionally absorb a significant amount of laser energy so as to provide a clinically significant heating of the tip so that tissue can be affected by contacting the tip to the tissue. As previously noted, the present invention is specifically designed to reflect substantially all light incident on the mirror so that there is no clinically significant heating of the tip.

A second feature of the present invention which contributes to avoiding undesired heating of the tip is the provision of the lateral flushing passageway 328 which allows surrounding ambient liquid to flow therethrough across the reflecting mirror surface 318. This contributes to avoiding heating of the tip in at least two ways. First, the flow of liquid through the flushing passageway 328 tends to carry away from the tip heated liquid adjacent thereto which is heated both by the laser energy passing through the liquid and by conduction from the mirror. Second, the flushing liquid flowing through the flushing passageway 328 tends to prevent organic debris from accumulating on the mirror surface 318.

It will be appreciated that it is particularly important to keep the reflecting mirror surface 318 as clean as possible. The surrounding liquid tends to have a significant amount of organic material therein, and to some extent over a period of time this material will cook onto the reflecting mirror surface 318 thus somewhat darkening it and reducing its reflectivity. That in turn will cause greater heating of the reflecting mirror surface 318 which in turn will cause additional organic material to cook onto the mirror. It will be appreciated that this condition feeds on itself and will rapidly progress to a tip failure if the mirror surface 318 is not kept clean.

A third feature which is particularly emphasized by the embodiment of FIGS. 18 and 19 can also significantly contribute to eliminating failure of the mechanical connection between the tip 306 and the fiber 16. The heating of the tip adjacent the mirror 318 and in the distally outer portions of the head 320 of tip 306 is not per sea problem. The problem only occurs when the proximal portions of the tip adjacent crimps 322 become sufficiently hot that thermal degradation of the outer protective jacket 304 of fiber 16 will occur. Thus, we have discovered that such mechanical failure can be greatly reduced by including in the tip 306 an intermediate portion 330 located between the reflecting mirror surface 318 and the crimps 322. This intermediate portion 330 must include sufficient material of sufficient thermal conductivity so as to dissipate to the surrounding liquid operating environment enough of the heat generated at the reflecting mirror surface means 318 so that the temperature at the crimps 322 remains sufficiently low that there is no failure of the mechanical attachment of the tip 306 to the outer protective jacket 304 of the fiber 16 during normal operation of the assembly 300. This construction of the intermediate portion 330 is dependent both upon the physical nature of the material and the amount of the material which is there present. Preferably, the entire tip 306 is constructed of 24-carat gold which has a very high thermal conductivity which will transfer heat energy to the surrounding liquid operating environment at a much more rapid rate than will many other materials from which tips have been built in the past, such as stainless steel. The amount of material in intermediate portion 330 is determined in part by the length of the portion 330 which has been chosen so as to provide the necessary outer surface area for radiating the heat which can be generated at mirror surface 318.

It is noted that the necessary size of the intermediate portion 330 is dependent upon the power density which is being applied to the tip. At lower power levels, heating of the tip is a less serious problem.

The increased length of the intermediate portion 330 of tip 306 as contrasted to prior designs provides several advantages. First, the longer distance provides better isolation of the heat source 318 from the crimps 322. Second, the additional length also gives more surface area for dissipation of heat to the surrounding liquid. Finally, the increased length of the tip provides room for additional crimps 322 to increase the strength of the overall mechanical connection.

In general, these several features which contribute to controlling heating of the tip 306 can be described as follows. The body 308, the crimping cylinder 310, the reflecting mirror surface 318 and the lateral flushing passageway 328 are arranged and constructed so as to provide a means for preventing thermal degradation of the outer protective jacket 304 at the crimps 322 and for thereby preventing failure of the mechanical attachment between the crimping cylinder 310 and the outer protective jacket 304.

It is noted that in the preferred embodiment of FIGS. 18 and 19, the crimping cylinder 310 is formed of 24-carat gold. Although certain prior art tips have utilized gold plating for their reflecting mirror surface, the tip of FIGS. 18 and 19 is the first to construct the entire tip of gold and particularly is the first to construct those portions of the tip which are mechanically attached to the fiber from gold. Traditional thinking has been that gold does not have sufficient mechanical strength to be utilized for the mechanical attachment of the tip to the fiber. Thus, typically prior designs have utilized stainless steel materials at the point of attachment. We have discovered, however, that the failure of a typical tip mounting to a fiber is due to the thermal degradation of the underlying outer protective jacket of fiber 16 and not to the mechanical strength of the tip itself. Physical examination of failed specimens has shown that the failure is a thermal decomposition of the polytetrafluoroethane material. The carbonaceous material in that outer protective coating 304 will soften, chemically degrade, char and become black from thermal decomposition. These events can initiate at a temperature of approximately 150° C.

Accordingly, we have discovered that the benefits of using gold for the crimping cylinder 310, namely the increased heat transfer and thus reduced heating of the gold, are much more important than the lesser mechanical strength of the gold. We have discovered that sufficient crimps 322 can be provided to provide sufficient mechanical attachment strength between the gold and the fiber thus providing a means of attachment which is much less susceptible to thermal failure than is a similar stainless steel structure.

The thermal conductivity of gold is 295 W. per meter degree K. This is contrasted to stainless steel which typically has a thermal conductivity of about 25.1 W. per meter degree K. Thus, the thermal conductivity of gold is approximately ten times greater than stainless steel and thus heat is transferred to the surrounding liquid environment approximately ten times faster by a gold tip than by a stainless steel tip. In general, the preferred materials for the tip 306 should have a thermal conductance of 150 W per meter degree K or greater. If a stainless steel body were used, then to obtain the same degree of thermal isolation of the crimp from the mirror, it would be necessary to increase the length of the body by a factor of about ten (295/25.1).

Another advantage of the use of solid gold for forming the tip rather than the use of gold plate on a tip made of a second material such as stainless steel is that many tips using gold plating have encountered failure of the gold plating at some stage during the operating procedure. With a solid gold tip, there is no danger that a plated gold mirror surface will deteriorate exposing non-gold material therebelow to corrosion, lessened reflection, and increased heating.

Another reason that gold is the preferred material for these tips is that the tip is being used in a corrosive environment of saline solution. Although other materials such as copper for example can provide good reflectance, those materials are not stable in a corrosive environment.

Other materials could be utilized depending upon the context in which the tip is used. If the tip is not being used in a corrosive environment, copper provides a good material since it, too, has a high thermal conductivity. Another material with an excellent thermal conductivity is diamond.

Lower purity golds such as 12-carat or 18-carat golds are not as desirable. These golds are formed by alloying of the gold material with copper or nickel. Although this alloying increases the hardness and mechanical strength of the material, it decreases the reflectivity of the material. This is undesirable since maximum reflectivity is necessary in order to minimize the heat generated at mirror 318 in the first place.

We have determined that forming of the mirror 318 by coining of a solid gold surface is preferable to the use of a plated gold surface for several reasons. First, the coining operation removes the surface roughness. Second, the coining operation improves the optical characteristics and chemical resistance of the gold surface. The coining operation increases the density of the subsurface layer of gold thus providing less surface area for chemical reaction. Also, the thin cold worked layer at the coined surface is more mechanically akin to the underlying bulk gold than is a plated gold layer and thus it is much less likely to delaminate or flake off.

EXAMPLE NO. 2

A number of tips constructed in accordance with FIGS. 18 and 19 were immersed in quiescent normal saline solution confined within an 8 mm. diameter channel bored through an Irish potato and lased with 1,064-μm Nd:YAG radiation at 60 or 90 W. The emerging beam intercepted by the potato tissue resulted in heating and coagulation of the tissue. Tips were powered continuously for fifteen minutes with a rotation of the tip of 90° every sixty seconds. Following the continuous lasing, the tips were inspected visually at 10× magnification and the optical reflectance at 1,064 mm compared with the value measured prior to lasing.

Reflectance measurements using 1,064-nm Nd:YAG laser radiation showed virtually negligible decreases from 92.6 to 89.6% and 93.2 to 87.8% upon fifteen minute lasing in quiescent saline solution at 60 and 80 W, respectively. During the latter eight to ten minutes lasing, the solution was observed to boil and to incorporate a sludgy residue of potato from the walls of the 8 mm bore. Visual examination of the gold mirror surface of the tips showed a thin hazy coating outside an approximately 1 mm diameter clear region centered upon the beam impact area on the reflecting mirror. Soaking the tip for approximately twenty minutes in 1 N nitric acid resulted in removal of the hazy coating, thus suggesting its organic nature deriving from the potato.

Rigorous mechanical flexure of the gold tips relative to each of these fibers disclosed no loosening. Lack of heat sinking of thermal energy from the tip to the surrounding fluid could be expected to have led to thermally induced degradation of the buffer polymer of the outer protective jacket 304 and loss of the competency of the mechanical connection between the tip 306 and the outer protective jacket 304. No evidence of thermally induced weakening of this mechanical connection or misalignment of the tip 306 and fiber 16 were discerned after the extended lasing in boiling solution.

The results of these tests can be summarized by saying that the tip 306, and particularly the intermediate portion 330 thereof, includes sufficient material of sufficient thermal conductivity to prevent failure of the mechanical attachment at crimps 322 due to thermal decomposition of the outer protective jacket 304 when the tip 306 is continuously lased at 80 W input power in a saline solution for a period of at least fifteen minutes.

Typical dimensions for a tip like that of FIGS. 18 and 19 designed for use with a 600 μm fiber having a 600 μm silica core, hard clad coat, and a 1,000 μm diameter buffer are represented in FIG. 19. The diameter of the body 308 is indicated by 332 and is preferably 0.087 inches. The diameter of the reduced diameter clamping cylinder 310 is identified as 334 and is preferably 0.068 inches. The overall length is identified as 336 and is preferably 0.700 inches. The distance from the proximal end to the center line of radial port 326 is identified as 338 and is preferably 0.6183 inches. The length from the proximal end to the shoulder 318 between counterbore 316 and main bore 314 is identified as 340 and is preferably 0.3456 inches. The distance from the proximal end to the shoulder between body 308 and crimping cylinder 310 is identified as 342 and is preferably 0.3063 inches. The main bore 314 is preferably 0.0360 inch and the counterbore 316 is preferably 0.0420 inch.

Thus it is seen that the apparatus and methods of the present invention readily achieve the ends and advantages mentioned as well as those inherent therein. While certain preferred embodiments of the invention have been illustrated and described for purposes of the present disclosure, numerous changes may be made by those skilled in the art which changes are encompassed within the scope and spirit of the present invention as defined by the appended claims.

What is claimed is:

1. An operating assembly for use in a liquid operating environment, comprising:
   a flexible elongated light transmitting fiber having a distal end portion with a distal fiber end defined thereon, said fiber including a core, a cladding surrounding said core, and an outer protective jacket surrounding said cladding; and
   a light reflecting tip including:
   a body;
   a reduced diameter hollow crimping cylinder extending proximally from said body;
   said body and said crimping cylinder having a body bore defined therein, said distal end portion of said fiber being received in said body bore;
   at least one crimp in said crimping cylinder, said crimp mechanically attaching said light reflecting tip to said outer protective jacket of said fiber;
   a reflecting mirror surface means defined on said body for laterally reflecting light from said fiber; and
   said body having a lateral flushing passageway means defined laterally through said body and intersecting said body bore, for permitting surrounding liquid to flow through said lateral flushing passageway means across said reflecting mirror surface means thereby aiding in cooling said tip.

2. The assembly of claim 1, wherein:
   said body, said crimping cylinder, said reflecting mirror surface means and said lateral flushing passageway means comprise a means for preventing thermal degradation of said outer protective jacket at said crimp and for thereby preventing failure of the mechanical attachment between said crimping cylinder and said outer protective jacket during normal operation of said assembly.

3. The assembly of claim 1, wherein:
   said body includes material of thermal conductivity of at least 150 W per meter degree K between said reflecting mirror surface means and said crimp to dissipate to said liquid operating environment the heat generated at said reflecting mirror surface means so that the temperature at said crimp remains below 150° C. so that there is no failure of the mechanical attachment of said tip to said outer protective jacket of said fiber during continuous lasing at 80 W input power in a saline solution for a period of at least fifteen minutes.

4. The assembly of claim 1, wherein:
   said body and said crimping cylinder are integrally constructed from a single piece of gold.

5. The assembly of claim 1, wherein:
   said tip is attached to said fiber solely by a plurality of said crimps in said crimping cylinder mechanically attaching said tip to said outer protective jacket of said fiber.

6. The assembly of claim 1, wherein said body is solid gold.

7. The assembly of claim 6, wherein said body is solid gold in excess of 99.9 percent purity.

8. The assembly of claim 6, wherein said reflecting mirror surface means is formed on said solid gold body by coining.

9. The assembly of claim 1, wherein said lateral flushing passageway means is free from communication with any source of flushing fluid other than surrounding liquid from said liquid operating environment.

10. The assembly of claim 1, wherein said crimping cylinder is formed of gold.

11. The assembly of claim 1, wherein said reflecting mirror surface means is constructed to reflect substantially all light falling thereon.

12. The assembly of claim 11, wherein said reflecting mirror surface means and said lateral flushing passageway means comprise a means for preventing any clinically significant heating of said tip.

13. The assembly of claim 1, wherein:
said lateral flushing passageway means extends laterally through said tip and has laterally opposite first and second flushing passageway end openings, so that said liquid passing through said lateral flushing passageway means flows in one of said first and second flushing passageway end openings and out the other of said flushing passageway end openings.

14. The assembly of claim 13, wherein:
said tip is generally cylindrical in shape; and
said lateral flushing passageway means extends diametrically through said tip.

15. The assembly of claim 1 wherein:
said tip is free from attachment to any structure other than said outer protective jacket of said fiber.

16. A light reflecting tip apparatus for mounting upon a distal end portion of a flexible elongated light transmitting fiber, comprising:
an elongated cylindrical body having a fiber receiving longitudinal opening means defined therein for receiving said distal end portion of said fiber, and having a lateral passageway defined diametrically therethrough and intersecting said longitudinal opening, said lateral passageway having diametrically opposite first and second end openings;
a reflecting mirror surface means defined on said body for reflecting light from said fiber laterally outward through said lateral passageway; and
wherein said lateral passageway provides a flushing means for permitting surrounding fluid to flow in one of said first and second end openings, then across said reflecting mirror surface means, then out the other of said first and second end openings to reduce collection of contaminants on said reflecting mirror surface means, said flushing means being free from communication with any source of flushing fluid other than said surrounding fluid surrounding said cylindrical body.

17. The apparatus of claim 16, wherein:
said fiber receiving longitudinal opening means of said cylindrical body is coaxial with said cylindrical body.

18. The apparatus of claim 16, wherein:
said reflecting mirror surface means is a means for reflecting substantially all light energy incident thereon from said fiber.

19. The apparatus of claim 18, wherein:
said reflecting mirror surface means is made of gold.

20. The apparatus of claim 19, wherein:
said body is solid gold.

21. The apparatus of claim 19, wherein:
said gold reflecting mirror surface means is coined.

22. An operating assembly for use in a liquid operating environment, comprising:
a flexible elongated light transmitting fiber having a distal end portion with a distal fiber end defined thereon; and
a light reflecting tip attached to said distal end portion of said fiber, said tip including a reflecting mirror surface spaced from said distal fiber end and so arranged and constructed as to laterally reflect light exiting said distal fiber end, said tip having a flushing passageway defined therein between said distal fiber end and said reflecting mirror surface so that surrounding liquid from said liquid operating environment may pass through said flushing passageway to carry away from said tip liquid heated by light passing from said distal fiber end to said reflecting mirror surface, said flushing passageway being free from communication with any source of flushing fluid other than said surrounding liquid from said liquid operating environment.

23. The assembly of claim 22, wherein said reflecting mirror surface is constructed to reflect substantially all light falling thereon.

24. The assembly of claim 23, wherein said reflecting mirror surface and said flushing passageway comprise a means for preventing any clinically significant heating of said tip.

25. The assembly of claim 22, wherein:
said flushing passageway extends laterally through said tip and has laterally opposite first and second flushing passageway end openings, so that said liquid passing through said flushing passageway flows in one of said first and second flushing passageway end openings and out the other of said flushing passageway end openings.

26. The assembly of claim 25, wherein:
said tip is generally cylindrical in shape; and
said flushing passageway extends diametrically through said tip.

27. The assembly of claim 22, wherein:
said tip is free from attachment to any structure other than said fiber.

28. A light reflecting tip apparatus for mounting upon a distal end portion of a flexible elongated laser light transmitting fiber, comprising:
a metal body having a reflecting mirror surface defined on said body and positioned to laterally reflect light from said fiber; and
means, operably associated with said metal body, for preventing clinically significant heating of said metal body, said means including a flushing passageway defined laterally through said metal body and passing across said reflecting mirror surface, said flushing passageway having first and second laterally opposite flushing passageway ends so that liquid surrounding said tip may pass in one of said first and second flushing passageway ends, then through said flushing passageway, then out the other of said first and second flushing passageway ends, said flushing passageway being free from communication with any source of flushing fluid other than said liquid surrounding said tip.

29. The apparatus of claim 28, wherein said reflecting mirror surface is constructed from a material selected from the group consisting of gold and platinum.

30. The apparatus of claim 28, wherein:
said metal body is entirely constructed from a material selected from the group consisting of gold and platinum.

31. The apparatus of claim 28, in combination with said fiber, wherein:
said metal body is attached to said fiber and is free from attachment to any structure other than said fiber.

32. The apparatus of claim 28, wherein:
said reflecting mirror surface is constructed to reflect substantially all laser light incident thereon.

33. A method of applying laser energy to a site within a patient's body to alter, remove or destroy tissue at said site, comprising:
(a) providing an operating assembly including:
a flexible elongated light transmitting fiber having a distal end portion with a distal fiber end defined thereon; and
a light reflecting tip attached to said distal end portion of said fiber, said tip including a reflecting mirror surface spaced from said distal fiber end, said tip having a flushing passageway defined therein between said distal fiber end and said reflecting mirror surface;
(b) inserting said operating assembly into a liquid operating environment within said patient's body;
(c) positioning said tip adjacent said site within said patient's body;
(d) transmitting laser light along said fiber, out said distal fiber end, and across said flushing passageway;
(e) then reflecting said laser light off said mirror surface and transmitting said reflected light through a portion of said flushing passageway out of said tip and onto said site within said patient's body; and
(f) flowing surrounding liquid solely from said liquid operating environment through said flushing passageway and across said reflecting mirror surface without providing any flushing liquid from any source other than said liquid operating environment, and thereby carrying away from said tip liquid heated by light passing from said distal fiber end across said flushing passageway to said reflecting mirror surface.

34. The method of claim 33, wherein:
step (e) includes reflecting substantially all laser light falling on said mirror surface.

35. The method of claim 34, wherein:
steps (e) and (f) prevent any clinically significant heating of said tip.

36. The method of claim 33, further comprising:
preventing any clinically significant heating of said tip.

37. The method of claim 33 wherein:
in step (a), said flushing passageway extends laterally through said tip and has laterally opposite first and second flushing passageway end openings; and
step (f) includes flowing said surrounding liquid from said liquid operating environment in one of said first and second flushing passageway end openings and out the other of said flushing passageway end openings.

38. The method of claim 33, wherein:
step (f) includes reducing collection of contaminants on said reflecting mirror surface by flushing said reflecting mirror surface with said liquid flowing through said flushing passageway.

* * * * *

UNITED STATES PATENT AND TRADEMARK OFFICE
CERTIFICATE OF CORRECTION

PATENT NO. : 5,370,649
DATED : December 6, 1994
INVENTOR(S) : William W. Gardetto, et al It is certified that error appears in the above-indentified patent and that said Letters Patent is hereby corrected as shown below:

On the title page, item [63], under "Related U.S. Application Data", delete "746,818" and insert —746,418—.

Column 9, line 9, delete "9,000 mm" and insert —9.000 mm— therefor.

Column 9, line 10, delete "2,000 mm" and insert —2.200mm—. therefor.

Column 15, line 1, delete "per sea" and insert —per se a— therefor.

Column 17, lines 11-12, delete "1,064 µm" and insert —1.064 µm— therefor.

Column 17, line 18, delete "1,064 mm" and insert —1.064 mm— therefor.

Column 17, line 20, delete "1,064 nm" and insert —1.064 nm— therefor.

Signed and Sealed this

Eleventh Day of April, 1995

Attest:

BRUCE LEHMAN

*Attesting Officer*   *Commissioner of Patents and Trademarks*